United States Patent [19]

Faust

[11] Patent Number: 5,353,837
[45] Date of Patent: Oct. 11, 1994

[54] QUICK-DISCONNECT VALVE

[75] Inventor: Valentine Faust, Bow, N.H.

[73] Assignee: Deka Products Limited Partnership, Manchester, N.H.

[21] Appl. No.: 887,732

[22] Filed: May 22, 1992

Related U.S. Application Data

[63] Continuation-in-part of Ser. No. 748,341, Aug. 22, 1991, Pat. No. 5,116,021, which is a continuation-in-part of Ser. No. 674,813, Mar. 22, 1991, abandoned, Ser. No. 673,835, Mar. 22, 1991, abandoned, Ser. No. 674,818, Mar. 22, 1991, Pat. No. 5,193,990, and Ser. No. 673,834, Mar. 22, 1991, abandoned, said Ser. No. 674,813, Ser. No. 673,835, Ser. No. 674,818, and Ser. No. 673,834, each is a continuation-in-part of Ser. No. 615,612, Nov. 19, 1990, abandoned, and Ser. No. 614,806, Nov. 19, 1990, abandoned, said Ser. No. 615,612, and Ser. No. 614,806, each is a continuation-in-part of Ser. No. 523,801, May 15, 1990, Pat. No. 5,088,515, and Ser. No. 345,387, May 1, 1989, Pat. No. 4,976,162, which is a continuation-in-part of Ser. No. 92,481, Sep. 3, 1987, Pat. No. 4,826,482, which is a continuation-in-part of Ser. No. 22,167, Mar. 5, 1987, Pat. No. 4,808,161, and Ser. No. 836,023, Mar. 4, 1986, Pat. No. 4,778,451.

[51] Int. Cl.$^5$ ............................ F16K 3/24; A61M 39/00
[52] U.S. Cl. ............................ 137/614.18; 251/149.7; 604/249; 604/905
[58] Field of Search ............ 137/614.18, 614.19; 251/149.6, 149.7; 604/249, 326, 905

[56] References Cited

U.S. PATENT DOCUMENTS

| | | | |
|---|---|---|---|
| 962,027 | 6/1910 | Kennedy | 251/149.3 |
| 2,299,643 | 10/1942 | Moody | 251/149.1 |
| 3,192,949 | 7/1965 | De See | 137/540 |
| 3,429,338 | 2/1969 | Mackal et al. | 137/543.23 |
| 3,563,267 | 2/1971 | Thompson | 137/614.19 X |
| 3,570,484 | 3/1971 | Steer et al. | 604/249 |
| 3,726,282 | 4/1973 | Patel | 604/99 |
| 3,806,086 | 4/1974 | Cloyd | 251/149.7 |
| 3,831,629 | 8/1974 | Mackal et al. | 137/525 |
| 4,143,853 | 3/1979 | Abramson | 251/149.1 |
| 4,167,204 | 9/1979 | Zeyra | 251/149.1 X |
| 4,344,435 | 8/1982 | Aubin | 604/246 |
| 4,387,879 | 6/1983 | Tauschinski | 251/149.1 |
| 4,421,296 | 12/1983 | Stephens | 251/149.7 |
| 4,429,856 | 2/1984 | Jackson | 251/149.1 |
| 4,506,691 | 3/1985 | Tseo | 137/1 |
| 4,535,820 | 8/1985 | Raines | 137/854 |
| 4,629,159 | 12/1986 | Wellenstam | 137/614.18 X |
| 4,683,916 | 8/1987 | Raines | 137/854 |
| 4,710,168 | 12/1987 | Schwab et al. | 604/99 |
| 4,915,351 | 4/1990 | Hoffman | 251/149.1 |
| 5,020,562 | 6/1992 | Richmond et al. | 137/15 |
| 5,147,333 | 9/1992 | Raines | 604/249 |
| 5,184,652 | 2/1993 | Fan | 604/249 X |

FOREIGN PATENT DOCUMENTS 655197 1/1963 Canada .

Primary Examiner—John Rivell
Attorney, Agent, or Firm—Bromberg & Sunstein

[57] ABSTRACT

A normally-closed valve that can be easily connected and disconnected. Disposed in the fluid passageway through the valve is a cylindrical member that may be moved between an open position and a closed position. A spring holds the member in the closed position, and a leur-type cannula may be inserted into the valve to push the member into the open position. Two sealing rings are mounted around the cylindrical member. These rings prevent flow through the valve when the member is in its closed position. Two sets of channels are placed in the walls of the passageway to permit flow around the sealing rings when the member is in its open position.

3 Claims, 5 Drawing Sheets

QUICK-DISCONNECT VALVE

This application is a continuation-in-part of application Ser. No. 748,341 (the "Parent Application"), filed Aug. 22, 1991, now U.S. Pat. No. 5,116,021 which is a continuation-in-part of application Ser. No. 674,813 (for Flow-Control Valve System), now abandoned, application Ser. No. 673,835 (for Constant-Pressure Fluid Supply System), now abandoned, application Ser. No. 674,818 (for Fluid Management System with Auxiliary Dispensing Chamber), now U.S. Pat. No. 5,183,990, and application Ser. No. 673,834 (for Membrane-Based Rotary Peristaltic Pump), now abandoned, each of which was filed Mar. 22, 1991 and each of which is a continuation-in-part of application Ser. No. 615,612 filed Nov. 19, 1990, (for Acoustic Volume Measurement with Fluid Management Capability), now abandoned, and application Ser. No. 614,806 filed Nov. 19, 1990 (for Integral Intravenous Fluid Delivery Device), now abandoned, which are continuations-in-part of application Ser. No. 523,801 filed May. 15, 1990 (for a Valve System with Removable Fluid Interface) now U.S. Pat. No. 5,088,515, and application Ser. No. 345,387 filed May 1, 1989, issued Dec. 11, 1990 as U.S. Pat. No. 4,976,162 (for an Enhanced Pressure Measurement Flow Control System), which is a continuation-in-part of application Ser. No. 092,481 filed Sep. 3, 1987, issued as U.S. Pat. No. 4,826,482, which is a continuation-in-part of application Ser. No. 022,167 filed Mar. 5, 1987, issued as U.S. Pat. No. 4,808,161, and application Ser. No. 836,023 filed Mar. 4, 1986, issued as U.S. Pat. No. 4,778,451. These related applications are hereby incorporated herein by reference.

TECHNICAL FIELD

The invention relates generally to valves that may be easily connected or disconnected, and more specifically to such valves employed in medical intravenous fluid delivery systems.

BACKGROUND OF THE INVENTION

Several prior art check valves, such as those shown in U.S. Pat. Nos. 5,020,562 to Richmond et al., 3,831,629 to Mackal et al., 3,570,484 to Steer et al., 3,429,338 to Mackal et al., and 3,192,949 to De See, normally prevent flow through the valve and allow flow when actuated by a cannula. Although these valves have pistons that move within the fluid passageway, sealing does not occur at a sealing ring mounted on the periphery of the piston adjacent the passageway wall, but rather at the end of the piston or on a shoulder of the piston (not at the periphery of the shoulder). Thus, these valves do not need channels to permit flow past the sealing ring when the valve is opened.

U.S. Pat. No. 4,683,916 to Raines shows a normally closed valve wherein sealing is accomplished by a disk, which is deformed, when a cannula is inserted into the valve, in order to permit flow through the valve.

U.S. Pat. No. 4,143,853 to Abramson also shows a normally closed valve. A disk having a central axially extending slit normally prevents flow through the valve, and when actuated by a cannula, permits flow through the opened slit.

SUMMARY OF THE INVENTION

The present invention provides a valve for normally preventing flow of fluid therethrough and permitting flow therethrough when actuated by a cannula. The valve has a fluid passageway disposed therethrough, and the passageway is bounded by a wall. One end of the passageway is adapted to receive a cannula; the other end of the passageway is preferably in fluid communication with an intravenous line.

Disposed in the passageway is a movable member, preferably cylindrical in shape. The movable member is displaceable in a direction parallel to overall fluid flow through the valve. The movable member may be displaced to an open position, wherein fluid may pass through the valve, or to a closed position, wherein fluid is prevented from passing through the valve. When the movable member is in the closed position, it is closer to the end of the passageway that receives the cannula, than when it is in the open position. The movable member may be moved from its closed position to its open position by a cannula inserted into the passageway.

A spring, or other biasing means, urges the movable member away from the open position towards the closed position, so that the valve is normally closed. A seal, mounted on the perimeter surface of the movable member, prevents flow between the passageway wall and the perimeter surface of the movable member when the movable member is in the closed position. A channel, mounted in the passageway wall, permits flow between the seal and the passageway wall when the movable member is in its opened position.

In a preferred embodiment of the invention, a second seal is also mounted on the perimeter surface of the movable member. This second seal also prevents flow between the passageway wall and the perimeter surface of the movable member when the movable member is in the closed position. The first seal is mounted closer to the end of the movable member that is pushed by the cannula than the second seal. A second channel is mounted in the passageway wall and permits flow between the second seal and the passageway wall when the movable member is in the open position.

DESCRIPTION OF SPECIFIC EMBODIMENTS

Figure 1:
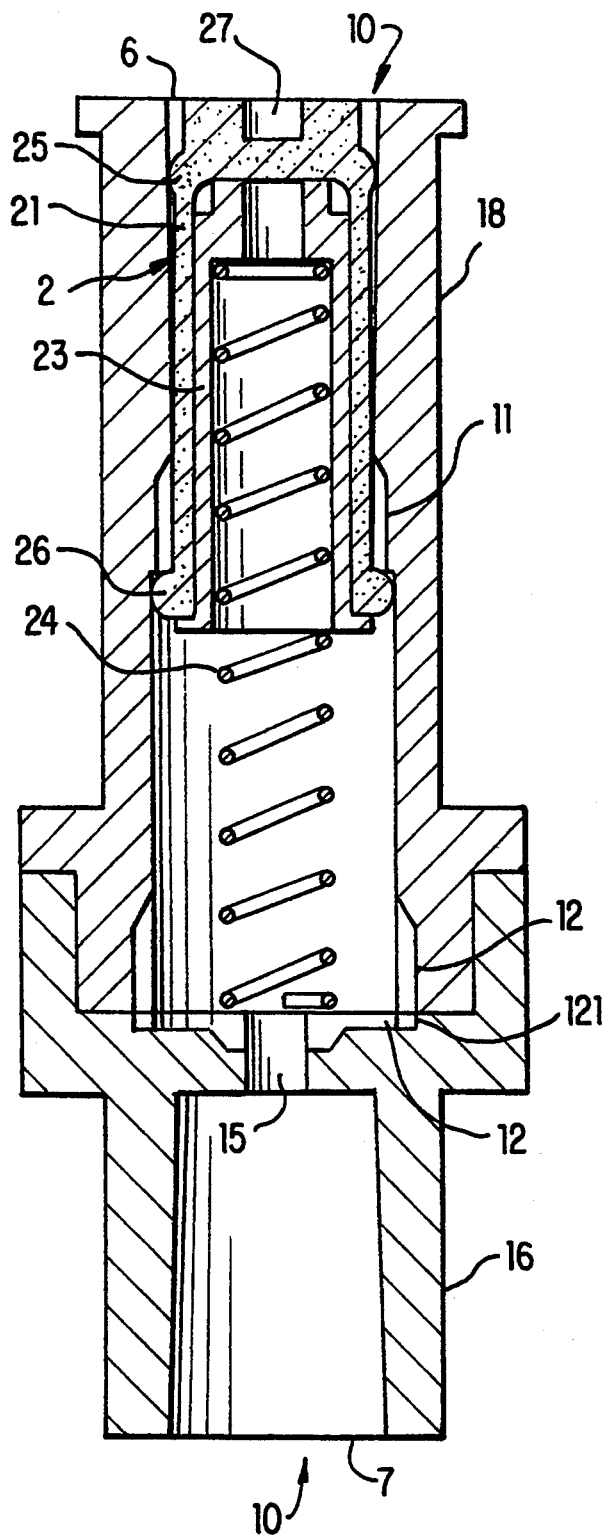
FIG. 1 is a cross-sectional view of a valve according to the present invention in the closed position.

The valve shown in FIG. 1 has a fluid passageway 10, having two ports 6 and 7. The wall of the passageway 10 may be formed by two parts, 16 and 18, making up the valve housing. The lower part 16 of the valve housing may be connected in fluid communication with an intravenous line and may be made an integral part of an integral intravenous fluid delivery device, such as that shown in application Ser. No. 07/614,806, referenced hereinabove. Thus, port 7 may be attached to an intravenous fluid line, and in such an arrangement, port 6 permits fluid to be introduced into the line or drawn from the line.

Figure 6:
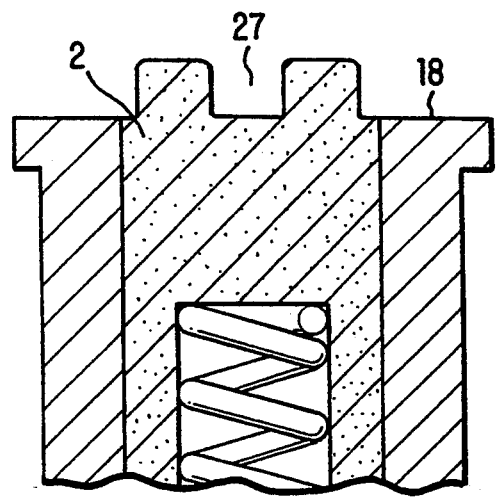
FIG. 6 shows a detail of a cross-section of a modified version of the value in the closed invention.
Figure 3C:
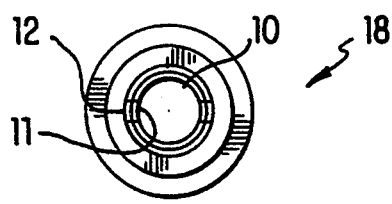
FIG. 3C is a bottom plan view of the housing portion shown in FIG. 3A.
Figure 5A:
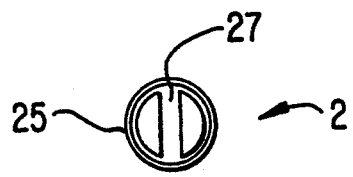
FIG. 5A is a top plan view of the piston.
Figure 5B:
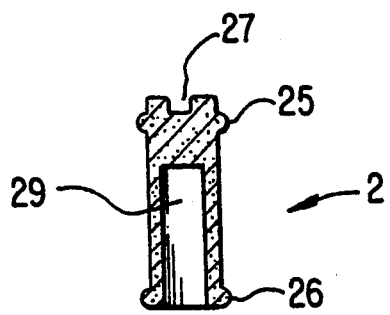
FIG. 5B is a cross-sectional view of the piston shown in FIG. 5A.

Disposed in the passageway 10 is a movable piston 2, which in one embodiment may be made of two components: a rigid inner piston 23, and a flexible, resilient sleeve which the inner piston 23 fits into snugly and which is preferably made of silicone. Alternatively, the whole piston 2 may be made of a single flexible, resilient material, as shown in FIG. 5B. The piston may be made slightly longer so that its top extends slightly beyond the top of the housing's upper portion 18, and so that the bottom of the channel 27 is flush with the top of the housing's upper portion 18, as shown in FIG. 6; such an alteration makes it easier to wipe and clean the top of the valve. Sealing protrusions 25 and 26 made of the resilient material are located at opposite ends of the piston 2 around its perimeter. The piston 2 is held in the closed position, shown in FIG. 1 by a spring 24, or other biasing means, as well as by fluid pressure in the intravenous line. In the closed position, two seals are formed between the piston 2 and the housing 18 by the sealing rings 25 and 26. The sealing rings 25 and 26 contact the housing wall 18 at the outermost perimeter of the sealing rings. These two seals prevent fluid from flowing through the valve, and therefore prevent the leaking of intravenous fluid from the intravenous line.

Figure 2:
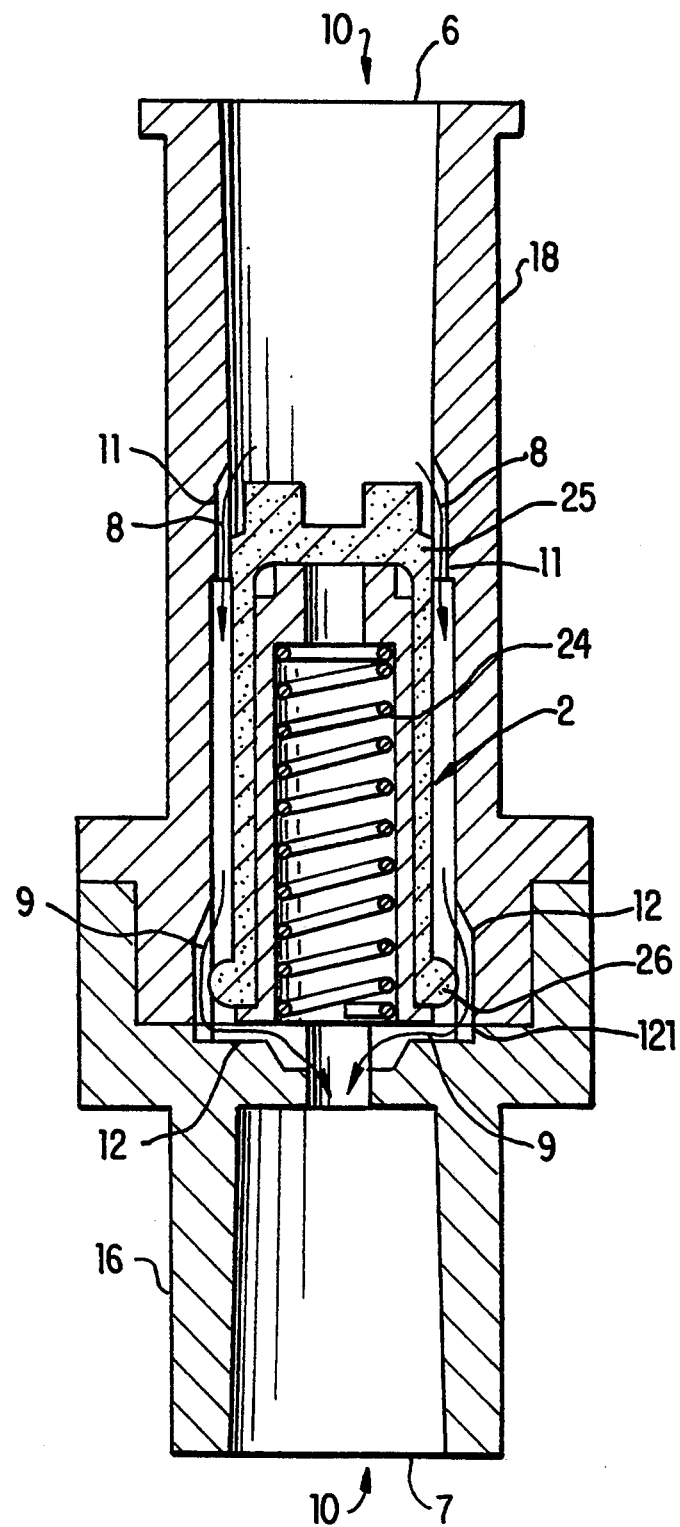
FIG. 2 is a cross-sectional view of the valve shown in FIG. 1 in the open position.
Figure 3A:
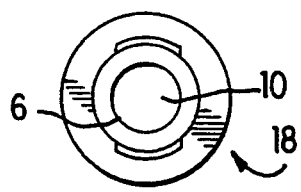
FIG. 3A is a top plan view of the valve housing's upper portion.
Figure 3B:
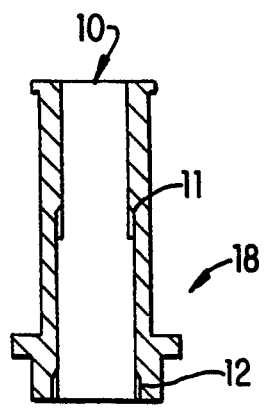
FIG. 3B is a cross-sectional view of the housing portion shown in FIG. 3A.

When a cannula is inserted into the external port 6 (as shown in FIG. 11 of the Parent Application), the piston 2 is pushed into the valve against the force of the spring 24, until the piston 2 reaches the open position shown in FIG. 2. The diameter of the external port 6 gradually decreases from the uppermost portion of the valve to the channel 11; this shape permits the use of a standard luer-type tapered cannula. (The description of the valve herein uses directional terms such as top, bottom, upper and lower in order to clearly explain the figures; the valve may, of course, be oriented in any direction and still work properly, and the use of such directional terms is not meant to imply otherwise.) Once the piston 2 is pushed into the open position, fluid may pass through the cannula, around the piston 2 and through the valve by means of a series of channels. A channel 27 on the top of the piston 2 permits fluid to flow from (or into) the inserted cannula and around the top of the piston 6, in a way similar to how fluid passes around the top of the pin shown in FIG. 11 of the Parent Application. Fluid may flow between the housing 18 and upper sealing ring 25 (which is compressed by the tapered walls of the fluid passageway, when the piston 2 is pushed into the open position) by passing through one or more upper channels 11. Likewise, fluid may flow between the housing 18 and 16, and lower sealing ring 26 by passing through one or more lower channels 12. The channels 11 and 12 provide fluid communication past the sealing rings when the piston 2 is in the open position. The channels 11 and 12 may be formed as tubes passing through the housing wall, but such a structure is more difficult to manufacture than the simple open-face grooves cut in the passageway walls, as shown in FIGS. 1 and 2. Between the channels 11 and 12 in the upper portion of the housing, the diameter of the passageway 10 increases so as to permit the lower sealing ring 26, and therefore the piston 2, to move up and down. The smaller diameter of the passageway at the location of the channels 11 prevents the lower sealing ring 26 from moving up too far, and thereby prevents the piston 2 from falling out of the housing 18.

Figure 4A:
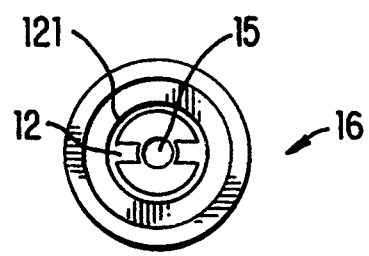
FIG. 4A is a top plan view of the valve housing's lower portion.
Figure 4B:
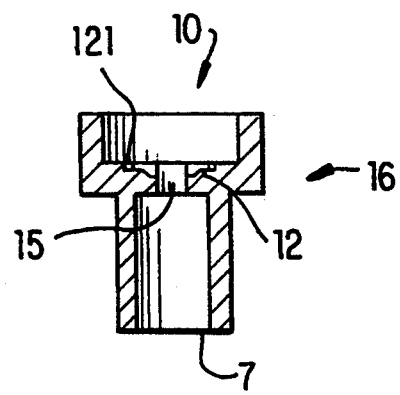
FIG. 4B is a cross-sectional view of the housing portion shown in FIG. 4A.
Figure 4C:
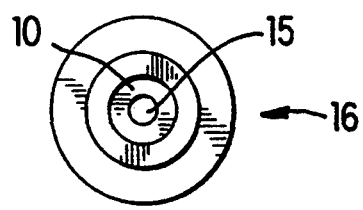
FIG. 4C is a bottom plan view of the housing portion shown in FIG. 4A.

As noted above, the housing may be made of two portions 16 and 18. In the embodiment shown in FIGS. 1 and 2, channel 12 is disposed in the inner walls of both of these portions. The cross-section of the housing shown in FIGS. 1 and 2 shows the two housing portions 16 and 18 aligned so that the section of channel 12 in the upper housing portion 18 is aligned with the section of the channel 12 in the lower housing portion 16. In order to avoid the necessity of having to align the upper and lower housing portions 18 and 16, an annular channel 121 may be located at the boundary between the upper and lower sections of channel 12. This annular channel 121 is also shown in FIG. 4A, which is a top plan view of the housing's lower portion. This annular channel 121 permits flow through channel 12 when the upper and lower sections of the channel 12 are not aligned.

When the cannula is removed from port 6, the spring 24 pushes the piston 2 back up to the closed position (as shown in FIG. 1). The spring 24 must apply enough force to overcome the friction between the housing 18 and the piston 2, in particular the piston's upper sealing ring 25, which is compressed when the piston 2 is in the open position (as shown in FIG. 2).

Figure 5C:
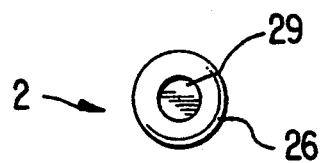
FIG. 5C is a bottom plan view of the piston shown in FIG. 5A.

FIGS. 3A–5C show various perspectives of three of the components that make up the valve shown in FIGS. 1 and 2. FIGS. 3A–4C show the two portions of the housing, and FIGS. 5A–5C show a piston made from a single material.

The valve shown in the figures and described above may be altered so that the upper sealing ring is attached to the passageway walls and the upper channels are placed in the piston. Unlike the preferred embodiments, where the upper sealing ring moves and the channels do not move, in this embodiment the upper channels move and the upper sealing ring does not move. This embodiment is not preferred, because it is much more difficult to clean properly—a very important consideration for intravenous fluid delivery systems. In this embodiment, the sealing ring is mounted some distance from the top of the valve. As the cannula is removed from the port and the piston returns to the closed position, fluid may collect in the space between the passageway wall and the piston where it is exposed to the air. In the preferred embodiment shown in the figures, the sealing ring 25 is located near the top of the valve when the valve is closed, and the fluid between the piston 2 and the passageway wall 18 is thereby sealed off from the air by the sealing ring 25, as shown in FIG. 1.

What is claimed is:

1. A valve for permitting flow of a fluid therethrough when actuated by a cannula, and otherwise preventing flow of fluid therethrough, the valve comprising:

a fluid passageway bounded by a wall and having first and second ports, the first port adapted to receive a cannula;

a movable member having first and second ends and a perimeter surface, the movable member being disposed in the fluid passageway, and being displaceable, in a direction parallel to overall fluid flow through the valve, to an open position, wherein fluid may pass through the valve, and to a closed position, wherein fluid is prevented from passing through the valve, such that when the movable member is in the closed position it is closer to the first port than when it is in the open position, and such that the movable member may be moved from the closed position to the open position by a cannula inserted through the first port;

biasing means for urging the movable member away from the open position towards the closed position;

first sealing means, located between the movable member and the passageway wall, for preventing flow between the passageway wall and the perimeter surface of the movable member when the movable member is in the closed position; and first channel means for permitting flow between the first sealing means and the passageway wall when the movable member is in its opened position;

wherein the first sealing means is mounted on the perimeter surface of the movable member, and the first channel means is mounted in the passageway wall; and further including second sealing means, mounted on the perimeter surface of the movable member, for preventing flow between the passageway wall and the perimeter surface of the movable member when the movable member is in the closed position, the first sealing means being mounted closer to the first end of the movable member and the first port than the second sealing means; and second channel means, mounted in the passageway wall, for permitting flow between the second sealing means and the passageway wall when the movable member is in the open position.

2. A valve according to claim 1, wherein the second port is in fluid communication with an intravenous line.

3. A valve according to claim 1, wherein the passageway is wider between first and second channel means than at the first channel means, so as to permit the second sealing means to move between the first and second channels, but not past the first channel means.

* * * * *